US008862219B2

(12) United States Patent
Garcia Molina et al.

(10) Patent No.: US 8,862,219 B2
(45) Date of Patent: Oct. 14, 2014

(54) RELATING TO BRAIN COMPUTER INTERFACES (75) Inventors: Gary Nelson Garcia Molina, Eindhoven (NL); Alphons Antonius Maria Lambertus Bruekers, Eindhoven (NL); Marijn Christian Damstra, Eindhoven (NL); Johannes Weda, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1207 days.

(21) Appl. No.: 12/680,230

(22) PCT Filed: Sep. 29, 2008

(86) PCT No.: PCT/IB2008/053951
§ 371 (c)(1),
(2), (4) Date: May 31, 2011

(87) PCT Pub. No.: WO2009/044325
PCT Pub. Date: Apr. 9, 2009

(65) Prior Publication Data
US 2011/0238685 A1    Sep. 29, 2011

(30) Foreign Application Priority Data

Oct. 4, 2007  (EP) ..................................... 07117858

(51) Int. Cl.
*A61B 5/04*     (2006.01)
*G06F 3/01*     (2006.01)
*A61B 5/0476*   (2006.01)
*G06Q 50/24*    (2012.01)

(52) U.S. Cl.
CPC .............. *G06F 3/015* (2013.01); *A61B 5/0476* (2013.01); *G06Q 50/24* (2013.01)
USPC ................................ 600/544; 600/545; 705/3

(58) Field of Classification Search
USPC .................. 600/544, 545; 707/69, 769; 705/3
See application file for complete search history.

(56) References Cited

U.S. PATENT DOCUMENTS

| 6,723,047 B1 | 4/2004 | Yamamoto |
| 2004/0097824 A1 | 5/2004 | Kageyama |
| 2006/0074822 A1 | 4/2006 | Baba |
| 2007/0032738 A1 * | 2/2007 | Flaherty et al. ............... 600/545 |

FOREIGN PATENT DOCUMENTS

| CN | 1833616 A | 9/2006 |
| JP | 03248541 A | 9/2003 |

(Continued)

OTHER PUBLICATIONS

Liao et al: "Transductive SVM for Reducing the Training Effort in BCI"; Journal of Neural Engineering, vol. 4, No. 3, Sep. 1, 2007, pp. 246-254.

(Continued)

Primary Examiner — Navin Natnithithadha
Assistant Examiner — Etsub Berhanu (57) ABSTRACT A method of creating a user profile for use in a brain computer interface includes performing a training exercise, measuring a user's brain signals during the training exercise, mapping specific signals of the user's brain signals to predefined mental task descriptions, and creating a user profile including the user's brain signals mapped to the mental task descriptions. The user profile so created can be used in a method of creating a brain computer interface for a user for an application. This method includes accessing a user profile including the user's brain signals mapped to mental task descriptions, accessing an application profile including a plurality of properties of the application, matching one or more mental task descriptions from the user profile to a respective property from the application profile, and creating a brain computer interface accordingly.

18 Claims, 8 Drawing Sheets (56) References Cited

FOREIGN PATENT DOCUMENTS

| JP | 2009531077 A | 9/2009 |
|----|--------------|--------|
| WO | 03073175 A2 | 9/2003 |
| WO | 2005039930 A2 | 5/2005 |
| WO | 2007096269 A1 | 8/2007 |

OTHER PUBLICATIONS

Thorpe et al: "Pass-Thoughts: Authenticating With Our Minds"; Proceedings of the New Security Paradigms Workshop (NSPW) 2005, pp. 1-11.

Vaughan et al: "Brain-Computer Interface Technology: A Review of the Second International Meeting"; IEEE Transactions on Neural Systems and Rehabilitation Engineering, vol. 11, No. 2, Jun. 2003, pp. 94-109.

Vaughan et al: "EEG-Based Communication: Prospects and Problems"; IEEE Transactions on Rehabilitation Engineering, vol. 4, No. 4, Dec. 1996, pp. 425-430.

Wolpaw et al: "Brain-Computer Interfaces for Communication and Control"; Clinical Neurophysiology, vol. 113 (2002), pp. 767-791.

Allison et al: "Brain-Computer Interface Systems: Progress and Prospects"; Expert Rev. Med. Devices, vol. 4 (4), 2007, pp. 463-474.

Ebrahimi et al: "Brain-Computer Interface in Multimedia Communication"; IEEE Signal Processing Magazine, Jan. 2003, pp. 14-24.

\* cited by examiner

| USER A | | |
|---|---|---|
| BRAIN SIGNAL 1 | TASK DESCRIPTION 1 | FATIGUE |
| BRAIN SIGNAL 2 | TASK DESCRIPTION 3 | FATIGUE |
| BRAIN SIGNAL 3 | TASK DESCRIPTION 4 | FATIGUE |
| BRAIN SIGNAL 4 | TASK DESCRIPTION 5 | FATIGUE |
| BRAIN SIGNAL 4 | TASK DESCRIPTION 6 | FATIGUE |

RELATING TO BRAIN COMPUTER INTERFACES

FIELD OF THE INVENTION

This invention relates to a method of and system for creating a user profile for use in a brain computer interface and to a method of and system for creating a brain computer interface for a user for an application.

BACKGROUND OF THE INVENTION

For many years people have speculated that electroencephalographic activity or other electrophysiological measures of brain function might provide a new non-muscular channel for sending messages and commands to the external world, commonly referred to as a brain computer interface (BCI). Over the past 20 years, productive BCI research programs have arisen. Encouraged by an improved understanding of brain functions, by the advent of powerful low-cost computer equipment, and by the growing recognition of the needs and potentials of people with disabilities, these programs concentrate on developing new communication and control technologies.

The most popular brain computer interfaces use electroencephalographic (EEG) activity recorded from the scalp, or single-neuron activity recorded within the cortex. These activities may be used in a computing environment to control cursor movement, select letters or icons, or may be used to operate neuro-prostheses. Central in each BCI is a translation algorithm that converts electrophysiological input from the user into output that controls one or more external devices. The operation of a BCI depends on an effective interaction between two adaptive controllers, the user who encodes his or her commands in the electrophysiological input provided to the BCI, and the BCI that recognizes the commands contained in the input and expresses them in device control. Further detail on BCIs can be found in J. R. Wolpaw, N. B., D. J. McFarland, G. Pfurtscheller, T. M. Vaughan, "Brain-computer interfaces for communication and control" Clinical Neurophysiology, 113 (2002) pages 767 to 791, and T. M. Vaughan, W. J. H., L. J. Trejo, W. Z. Rymer, "Brain-Computer Interface Technology: A Review of the Second International Meeting" IEEE Transactions on Neural Systems and Rehabilitation Engineering, 2003 11(2) pages 94 to 109.

BCIs may be provided to individuals with severe disabilities to improve their quality of life. Brain signals may, for example, be capable of providing enhanced control of devices such as wheelchairs, vehicles, or assistance robots for people with disabilities. As BCI technology improves it will probably expand to serve people with less severe disabilities, partial disabilities, or no medical disabilities at all. For example, BCIs could be used to monitor attention in long-distance drivers or aircraft pilots. BCIs might be used to control robots that function in dangerous or inhospitable situations. In other applications, BCIs might be used to provide additional control in video games or to create neural art and music.

The applications domain for BCIs can be seen as a continuum that runs from a binary switch (one bit, on or off) at one end to analog complex robotics at the other. Current BCIs have maximum information transfer rates of up to 25 bits/min. Achievement of greater speed and accuracy requires improvements in signal acquisition and processing, in translation algorithms, and in user training. The choice of BCI signals is affected by the application. For precise control functions, such as rapid motion of physical devices, the relatively slow changes of some EEG signals may be inadequate, whereas the more rapid dynamics of neuronal spike trains may suffice. However, such a choice forces another trade-off: surface electrodes are convenient and involve little risk whereas implantation of electrodes in the brain is invasive and, therefore, involves more risk.

Prior to a proper usage of a BCI by an individual user, an extensive training is required. First the user has to learn how to modulate their brain activity such that the proper electrophysiological signals are generated, and in addition, the BCI being used has to log many signals of the user and design a model or extract features. However, electroencephalogram (EEG) signals are naturally non-stationary, different from subject to subject and usually very noisy since they are contaminated with various artifacts such as electromyogram (EMG) and electrooculogram (EOG) signals. An electromyogram (EMG) detects the electrical potential generated by muscle cells when these cells contract, and also when the cells are at rest. Electrooculography is a technique for measuring the resting potential of the retina. It can be used to detect eye movements, and the adaptation of the eye to changing light conditions.

Both the signal variability and the noises may considerably distort the performance of an EEG classifier. Therefore, for many BCI systems, a tedious and time-consuming training process is usually needed for learning the specific characteristic of the brain signals; see for example X. Liao, D. Y., C. Li, "Transductive SVM for reducing the training effort in BCI" Journal of Neural Engineering, 2007 4(3), pages 246 to 254. In general the subject experiences the training for a BCI as taking too much time, boring and annoying. In some experiments even the offering of a monetary award to adults did not significantly reduce the training time whereas the offering of candy to children was successful. Especially for disabled or elderly people the training is very much a significant burden.

SUMMARY OF THE INVENTION

It is therefore an object of the invention to improve upon the known art.

According to a first aspect of the invention, there is provided a method of creating a user profile for use in a brain computer interface comprising performing a training exercise, measuring a user's brain signals during the training exercise, mapping specific signals of the user's brain signals to predefined mental task descriptions, and creating a user profile comprising the user's brain signals mapped to the mental task descriptions.

According to a second aspect of the invention, there is provided a system for creating a user profile for use in a brain computer interface comprising a training unit arranged to perform a training exercise, a head unit arranged to measure a user's brain signals during the training exercise, and a processing function arranged to map specific signals of the user's brain signals to predefined mental task descriptions, and to create a user profile comprising the user's brain signals mapped to the mental task descriptions.

According to a third aspect of the invention, there is provided a computer program product on a computer readable medium for creating a user profile for use in a brain computer interface, the product comprising instructions for performing a training exercise, measuring a user's brain signals during the training exercise, mapping specific signals of the user's brain signals to predefined mental task descriptions, and creating a user profile comprising the user's brain signals mapped to the mental task descriptions.

According to a fourth aspect of the invention, there is provided a method of creating a brain computer interface for a user for an application comprising accessing a user profile comprising the user's brain signals mapped to mental task descriptions, accessing an application profile comprising a plurality of properties of the application, matching one or more mental task descriptions from the user profile to a respective property from the application profile, and creating a brain computer interface accordingly.

According to a fifth aspect of the invention, there is provided a system for creating a brain computer interface for a user for an application comprising a database arranged to store a user profile comprising the user's brain signals mapped to mental task descriptions and an application profile comprising a plurality of properties of the application, and a processor arranged to access the user profile and the application profile, to match one or more mental task descriptions from the user profile to a respective property from the application profile, and to create a brain computer interface accordingly.

According to a sixth aspect of the invention, there is provided a computer program product on a computer readable medium for creating a brain computer interface for a user for an application, the product comprising instructions for accessing a user profile comprising the user's brain signals mapped to mental task descriptions, accessing an application profile comprising a plurality of properties of the application, matching one or more mental task descriptions from the user profile to a respective property from the application profile, and creating a brain computer interface accordingly.

Owing to the invention, it is possible to overcome the problems associated with the conventional usage of brain computer interfaces, which require extensive training, which takes a considerable amount of time and is boring, annoying and cumbersome. The invention provides a solution via the separation of the training and usage of a BCI into two parts: a generic training, and the usage. The training may involve a competitive element to motivate the user, and may focus of speed and accuracy. The measured brain signals are mapped onto mental task descriptions, and stored in a database. In the usage of the BCI, this database is used to map the mental task descriptions and related brain signals onto specific features of functions of the application. In this way the generic training only has to be performed once, and different applications can be controlled without individually learning/training them extensively. This constitutes a clear usability improvement for BCIs.

The principal advantage delivered by the invention is that there is no longer any need for the user to repeat training tasks for different applications. A user can participate in a single training session and this will be used to generate a user profile. This profile may contain, for example, details that the user can perform three different tasks in a steady and repeatable manner, and that these are then defined in the user profile. When a user is to be setup to use a new application, then a mapping occurs from the functions of that application to the content of the user profile. In the example above, then the mapping will take three of the functions of the new application and map these to the three contained in the user profile for the specific user. The user profile can also include a set of user preferences, for example, the user prefers certain mental tasks for accomplishing certain activities, and/or the user gets tired easily.

Brain signals are proven to be personal to some extent, and therefore in principle can be used for the authentication or identification of individuals, for example as shown in J. Thorpe, P. C. v. O., A. Somayaji, "Pass-thoughts: Authenticating with Our Minds" in ACSA 2005 New Security Paradigms Workshop 2005 Lake Arrowhead, Calif., USA. This invention is not about authentication or identification but this property also indicates that training is per user individually.

Advantageously, the training further comprises measuring a user's fatigue during the training exercise, and further comprising recording information relating to the measured fatigue in the user profile. Recording information about the user's fatigue improves the ultimate performance of the brain computer interface, as the mapping of the user profile to the new application can take into account the levels of fatigue that are associated with the specific tasks recorded in the user profile that the user can perform. For example, a user may be able to perform task A very accurately, but rapidly becomes fatigued and the performance deteriorates, whereas task B may be performed with a margin of error of 10%, but the user is able to maintain this level of performance over a longer period. When the mapping of the new application takes place, these fatigue levels can be used to determine which functions of the new application are matched to which task. For example, an application may indicate that function X is not so common in the application, but requires a high degree of accuracy, so this can be mapped to task A. Similarly, a high frequency function Y can be mapped to task B for which the user is less likely to suffer fatigue.

The training can also preferably be arranged to further comprise terminating the training exercise when the measured fatigue exceeds a predetermined threshold. Since fatigue is being measured during the creation of the user profile, this can also be used to control the length of time that the user is monitored to produce the user profile. This results in a user profile containing tasks that are highly likely to be consistently accurate in representing the performance of the user, as they have not created the user profile while fatigued.

Ideally the methodology also further comprises receiving manual input defining restrictions in relation to the predefined mental descriptions, and recording the manual input in the user profile. It is useful to be able to have user input to amend the user profile. This can be provided by a suitably qualified technician or medical practitioner. This will allow amendment of the user profile to take into account aspects such as safety and will ensure that an application that is mapped to a user profile does not place undue stress on the user. For example, a specific task that the user can perform may have limitations added to it by a doctor, who ensures that an application will not continue to operate after a point at which it would cause stress to the user.

Embodiments of the present invention will now be described, by way of example only, with reference to the accompanying drawings.

DETAILED DESCRIPTION OF THE EMBODIMENTS

The invention is based on the recognition that training and usage of a brain computer interface can be two activities that are completely separated in time. The following description consists of two parts: the first relates to the training and the second relates to the usage of a brain computer interface. In both cases, the purpose is to reduce the required training time that a user must undergo and as a consequence reduce boredom and improve convenience for the subject.

Figure 1:
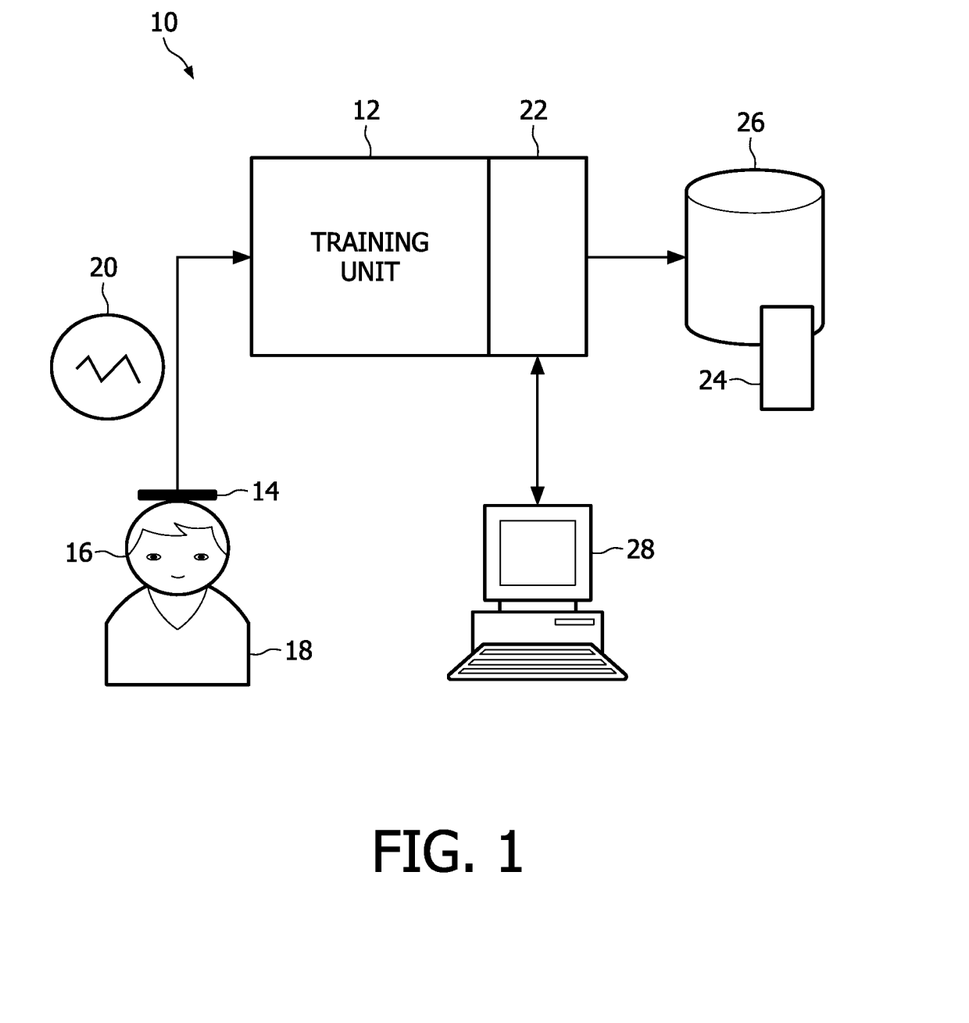
FIG. 1 is a schematic diagram of a system for creating a user profile for use in a brain computer interface.

FIG. 1 shows the basic scheme for training a user in relation to the creating of a brain computer interface. This Fig. shows a system 10 for creating a user profile for use in a brain computer interface. A training unit 12 is connected to a head unit 14. The head unit 14 comprises electrodes that are in contact with the scalp 16 of a subject 18, for example, by means of a cap with multiple electrodes, to measure brain signals 20 from specific parts of the brain of the user 18. In addition, the training unit 12 is arranged to perform a training exercise and interacts with the subject 18 to influence the brain signals 20. This interaction in a preferred embodiment consists of two parts. Firstly, the subject 18 can operate input devices such as a keyboard, mouse, special buttons, and various types of sensors, and secondly, the subject 18 is exposed to one or more outputs such as video, sound, smell and vibrations. The head unit 14 is arranged to measure the user's brain signals 20 during the training exercise.

Connected to the training unit 12 is a processing function 22 which is arranged to map specific signals of the user's brain signals 20 to predefined mental task descriptions, and to create a user profile 24 comprising the user's brain signals 20 mapped to the mental task descriptions. As a result many brain signals 20 and related data are stored in a database 26. Such a database typically contains a collection of mental task descriptions (MTD) and the related signals, extracted features and/or fitted models (SFM).

The purpose of the training is, as mentioned before, to create a database 26 that typically contains a collection of mental task descriptions (MTD) and the related signals, extracted features and/or fitted models (SFM). The user 18 is asked to perform a specific mental task and the measured related signals are stored. As an alternative, or in addition, special features can be extracted from the signals or some models can be trained.

During such training an effort can be made to make it less boring or annoying. As an example the subject 18 can be provided with a visual/auditory representation of his/her earlier measurements and the given task is to improve their performance. Also, the subject 18 can be provided with measurements of other (perhaps expert) users and encouraged to mimic their performance as closely as possible. Some tasks may focus on speed or accuracy to challenge the subject 18. If the subject 18 feels comfortable, it is possible to continue the training with a large variety of mental tasks. The final collection may be more extensive than required for a particular application. The set of MTDs and related SFMs may cover a wide range of potential applications and preferences.

The user profile 24 is specific to the user 18, and defines the mental tasks (MTD) that the user can undertake consistently and to a required level of accuracy. Each mental task description is stored in the user profile 24 with a corresponding set of the user's brain signals mapped to those tasks. Essentially the user profile 24 is storing the tasks that the user is able to carry out competently and can server as the basis for a functioning brain computer interface. The user profile may store only a small number of specific tasks and associate brain signals, such as three such tasks. However this will be sufficient to operate a very large number of potential applications, in a BCI environment.

The processing function 22 can be further arranged to measure the user's fatigue during the training exercise. This can be achieved, for example, by monitoring a repeated task, and noting the change in the user's brain signals 20 over a period of time. If the user 18 is taking longer to perform a specific task, or is performing the task with an increasing margin of error, then this would indicate that the user is becoming tired. The processing function 22 is further arranged to record information relating to the measured fatigue in the user profile 24. This information could take the form of time information about a specific task, such as a statement that indicates that user 18 can only perform the task for time t, or may record that the user 18 can only perform the respective task for a specific number of times. The fatigue information may also include details of margins of error, effectively stating which tasks can be carried out with a high degree of certainty, and which are likely to produce error results or are undetectable occasionally.

The processing function 22 can also be further arranged to terminate the training exercise when the measured fatigue exceeds a predetermined threshold. This allows the user 18 to continue the training exercise for as long as possible without tiring the user 18, but while nevertheless gathering useful information about the tasks that the user 18 can complete. The user profile 24 is expanded to include the largest number of tasks that the user 18 is able to carry out effectively.

The system 10 also further comprises a user interface 28 arranged to receive manual input defining restrictions in relation to the predefined mental task descriptions, wherein the processing function 22 is further arranged to record the manual input in the user profile 24. This allows a suitable doctor to examine and, if necessary, amend the profile 24 according to whether in the professional opinion of the doctor, limits should be placed on certain of the tasks recorded in the user profile 24, in order to protect the well-being of the user 18.

Figure 2:
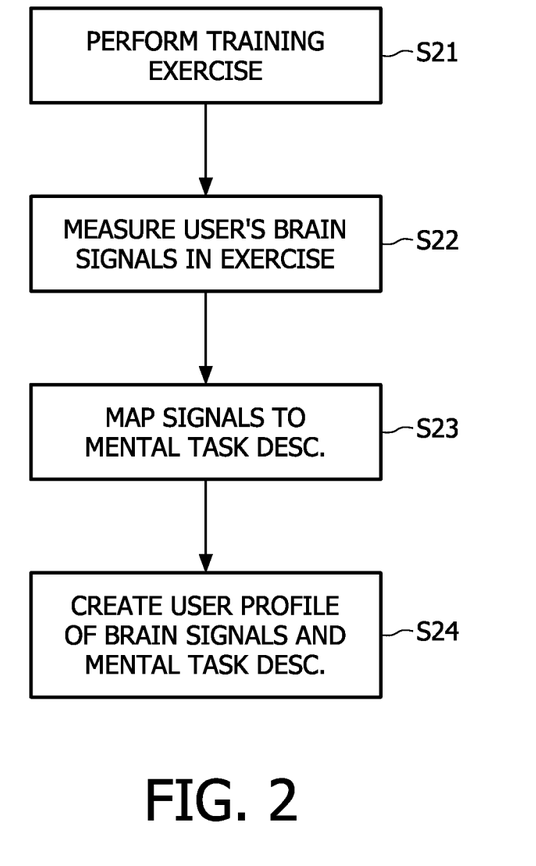
FIG. 2 is a flowchart of a method of creating the user profile.

FIG. 2 summarises the method of generating the user profile 24. A method of creating the user profile 24 for use in a brain computer interface comprises performing (step S21) the training exercise, measuring (step S22) the user's brain signals 20 during the training exercise, mapping (step S23) specific signals of the user's brain signals 20 to predefined mental task descriptions (MTD), and creating (step S24) the user profile 24 comprising the user's brain signals mapped to the mental task descriptions.

Figure 3:
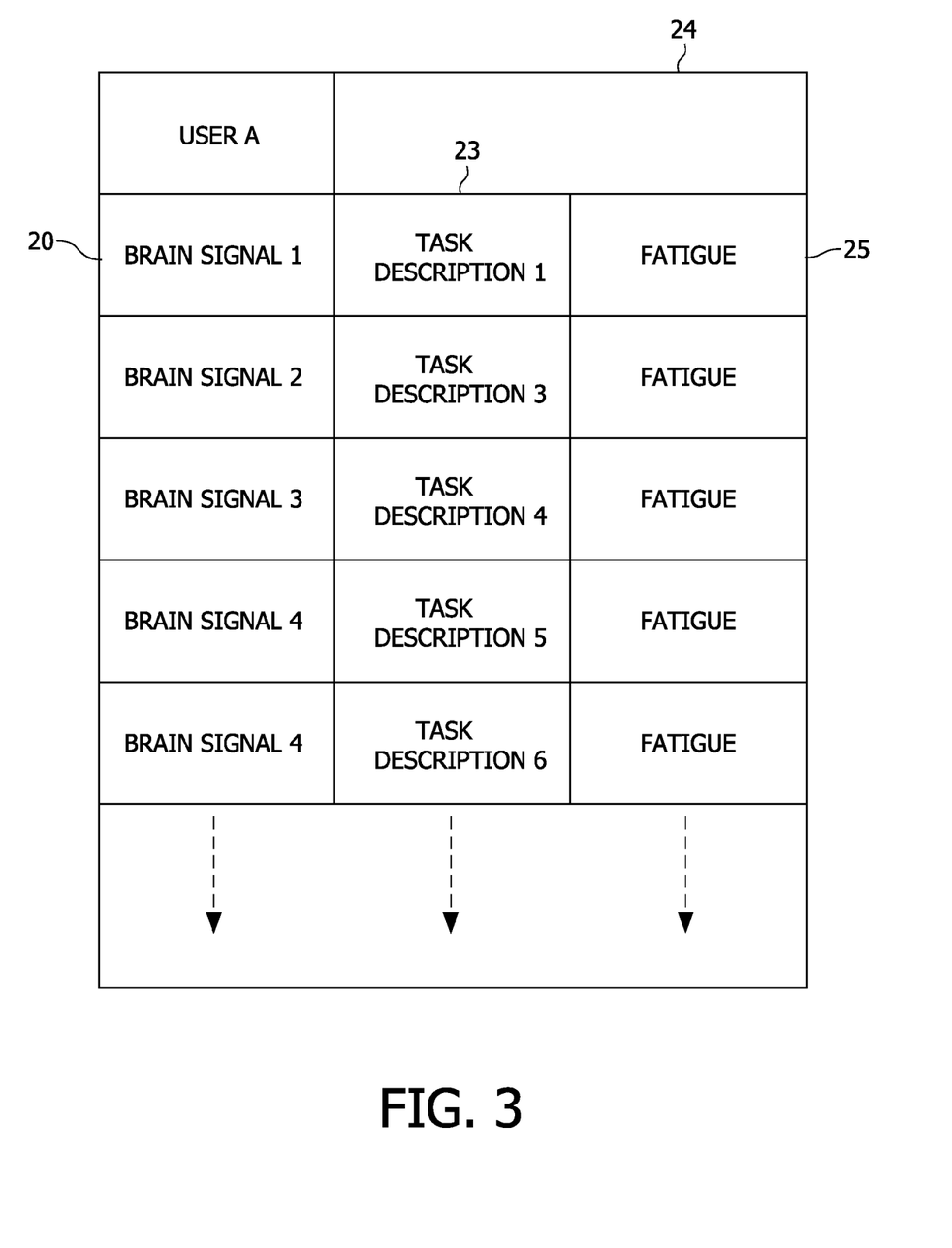
FIG. 3 is a schematic diagram of the user profile.

FIG. 3 shows a generated user profile 24 in more detail. This profile 24 is for user A, and comprises a series of brain signal measurements 20 mapped to specific mental task descriptions 23. Included with each pair of mapped signal 20 to mental task description 23 is a respective fatigue measurement 25. The fatigue measurement 25 could be something as simple as the number of times that the user 18 can perform the specific brain signal 20 within a predefined accuracy (such as +/−5%). In this example of the profile 24, it can be seen that the user 18 has been unable to perform mental task description number 2 to a sufficient level of accuracy, and so no brain signal 20 has been recorded in the profile 24 as mapping to this task description 23.

The various mental task descriptions 23 describe tasks such as on/off, yes/no, selection of compass points, or movement of a slider etc., which are needed to control an application in a very generalised sense or comprise a reference to such a task in the database 26. Task descriptions 23 can relate to the same function, for example a binary task description (switching between two states) could occur in different tasks 23, but have different brain signals 20 and fatigue levels 25 associated with them. The user 18 may be able to perform a first binary task with high degree of accuracy, but become tired relatively quickly, whereas a second binary task may have a lower accuracy, but the user 18 is able to perform this second task for a much larger number of times, before becoming tired.

In this way, the user 18 performs the various predefined training exercises, and their user profile 24 is generated accordingly. This profile 24 defines the user's ability to perform certain generalised mental tasks 23 and advantageously includes the fatigue information 25 for each respective task 23. The user profile 24 may comprise a long list of tasks 23 or may only contain two or three tasks, depending upon the individual user 18. The user profile 24 defines the extent that the specific user 18 can perform individual tasks 23 with a sufficient level of repeatability and accuracy to be useful in their deployment in a real application.

Figure 4:
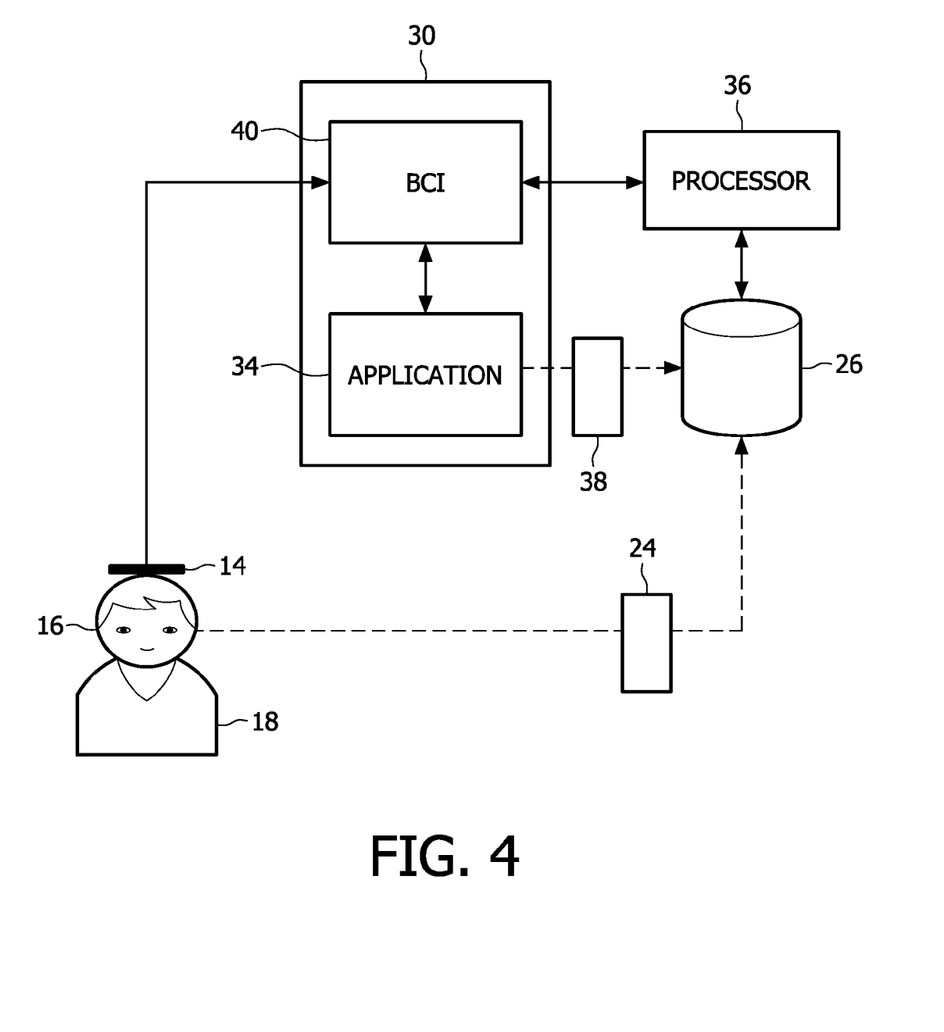
FIG. 4 is a schematic diagram of a system for creating a brain computer interface.

FIG. 4 illustrates the application of the generated user profile 24 in a practical example using a device 30, which might be a powered wheelchair for example. This device 30 includes a brain computer interface 40 and an application 34. The system for creating the brain computer interface 40 for the user comprises the database 26 which is storing the user profile 24 (comprised of the user's brain signals 20 mapped to mental task descriptions 23) and an application profile 38 comprising a plurality of properties of the application 34, and a processor 36 arranged to access the user profile 24 and the application profile 38, to match one or more mental task descriptions 23 from the user profile 24 to a respective property from the application profile 38, and to create a brain computer interface 40 accordingly.

In providing a system for using the BCI 40, the primary feature is to provide a device 30 that in principle can be (partly) operated by means of a BCI with the following features (as shown in FIG. 4). The application profile 38 is available that describes the types of control signals that are required to control the device 30 by means of the BCI. This description may be very brief like "there is a single on/off function", or exhaustive, for example a long list of actions including possible alternatives and other options. The user profile 24 is available that describes the preferences of the specific user 18 to control a particular BCI, and both profiles 24 and 38 are provided to the database 26 where a set of MTDs and related SFMs are stored. As a result the device 30 receives the required information from the database to optimally program the device.

In conclusion, the BCI 40 in the device 30 is provided almost immediately with information that is obtained during possibly multiple lengthy training sessions, required for this particular BCI, for this particular user, for this particular task. Once the BCI 40 is in use, the database 26 with MTDs and SFMs may be updated to improve future BCI applications for this user 18. This updating process may run in the background. The user profile 24 may be simply input using a graphical user interface or it can be stored on a smart card.

Figure 5:
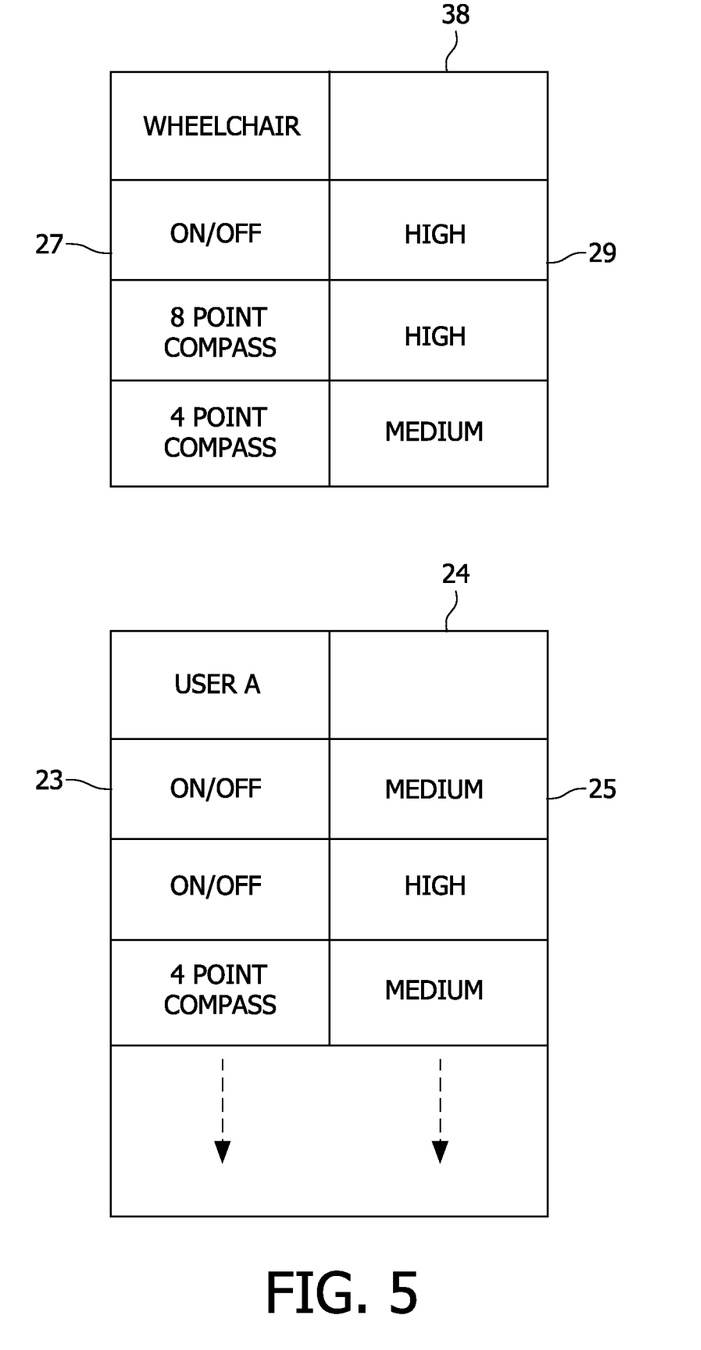
FIG. 5 is a schematic diagram of the user profile being matched to an application profile.

FIG. 5 illustrates the matching process that is used to generate the BCI 40 for the specific application of the wheelchair. The application profile 38 for the wheelchair contains three properties 27, being an on/off command (for turning the wheelchair on and off), an 8 point compass property (for moving the wheelchair), and a 4 point compass property (again for moving the wheelchair). Each property 27 also has respective accuracy information 29, which defines the desired level of accuracy needed to perform the property 27. Fatigue information could also be included within the accuracy information 29. In the same manner as the user profile 24, the properties 27 may not be explicitly stated, but may contain a numeric reference to an entry in the database 26.

The relevant entries in the user profile 24 of user A are shown. The user 18 has two on/off tasks 23 that they can perform, with different fatigue/accuracy levels 25. The user 18 can also perform the 4 point compass task 23, but cannot perform the 8 point compass task 23. This task 23 is not present in their profile 24. During the training stage, the user 18 could not perform this task 23 to a sufficient level of accuracy, and it was therefore not added in to their profile 24. The user 18 can perform the 4 point compass task 23 to a medium level of accuracy/fatigue 25.

When the BCI 40 is to be created for the specific user 18 for the specific wheelchair applisation, then the matching of the mental task descriptions 23 to respective properties 27 in the application profile 38 takes place. In this example, the second task 23 in the user profile 24 is matched to the first property 27 in the application profile 38, and the third task 23 in the user profile 24 is matched to the third property 27 in the application profile 38. In this way a BCI 40 is created, which allows the user 18 to control the wheelchair. The property 27 of the 8 point compass could not be matched, but the presence of the 4 point compass task 23 in the user profile 24 is sufficient to provide a working BCI 40, for the user 18.

The invention can be used in any device 30 that at least has some BCI for controlling the application 34. This technology may be used in the field of assisting disabled persons but also in the field of entertainment. The main advantage is that the required training is shorter and less (or even not at all) boring nor annoying. The invention provides a system for training a BCI where in a training session a collection of mental task descriptions (MTD) and the related signals, extracted features and/or fitted models (SFM) are obtained from a subject 18 and stored in a database 26 and later when this is to be used, a application profile 38 for a device is obtained and used to select data from the database 26 to program the BCI 40 in the device 30.

Figure 6:
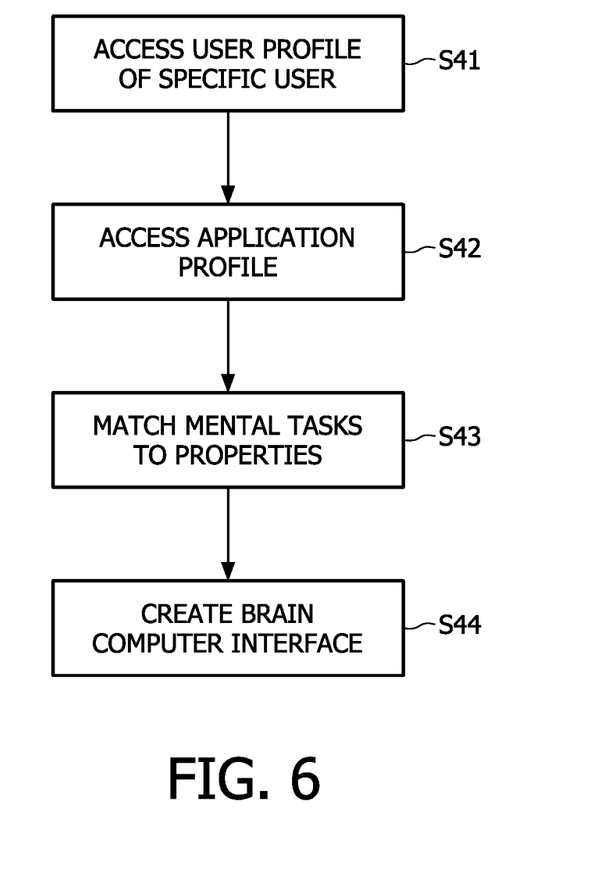
FIG. 6 is a flowchart of a method of creating the brain computer interface.

FIG. 6 summarises the method of creating the brain computer interface 40 for the user 18 for the application 34. The method comprises the steps of accessing (step S41) the user profile 24, which comprising the user's brain signals 20 mapped to mental task descriptions 23, accessing (step S42) the application profile 38 comprising a plurality of properties of the application 34, matching (step S43) one or more mental task descriptions 23 from the user profile 24 to a respective property 27 from the application profile 38, and creating (step S44) a brain computer interface 40 accordingly. Once the user profile 24 has been created for the user 18, it can be used again and again to generate a personalised brain computer interface 40, for the individual user 18 for a specific application 34. This is done automatically, and ensures that the user 18 does not have to redo training every time they wish to use a new application 34.

The processor 36 is mapping the known user capabilities (embodied in the user profile 24) to the functions of the application 34 (as defined by the application profile 38). For example, the application 34 may define within the profile 38 ten functions that the specific application provides, whether that application relates to a piece of hardware such as a wheelchair, or to a software function such as an email application. However the specific user profile 24 for the user 18 may define only five tasks that that user 18 can perform to a satisfactory level. In this case the processor 36 is choosing five of the ten properties 27 in the application profile 38 to match up to the mental task descriptions 23 in the user profile 24. This is then used to configure the brain computer interface 40.

As discussed above, in relation to the creation of the user profile 24, details about the user's levels of fatigue can be recorded in the user profile 24. This can be accessed by the processor 36 and used in the process of the matching of the mental task descriptions 23 to the properties of the application 34. The application profile 38 may specify certain of the functions that will be used most frequently, and which require the most accuracy, and so on. This is taken into account by the processor 36, when the decisions are made about the specific matching that occurs in relation to the present application 34.

Figure 7:
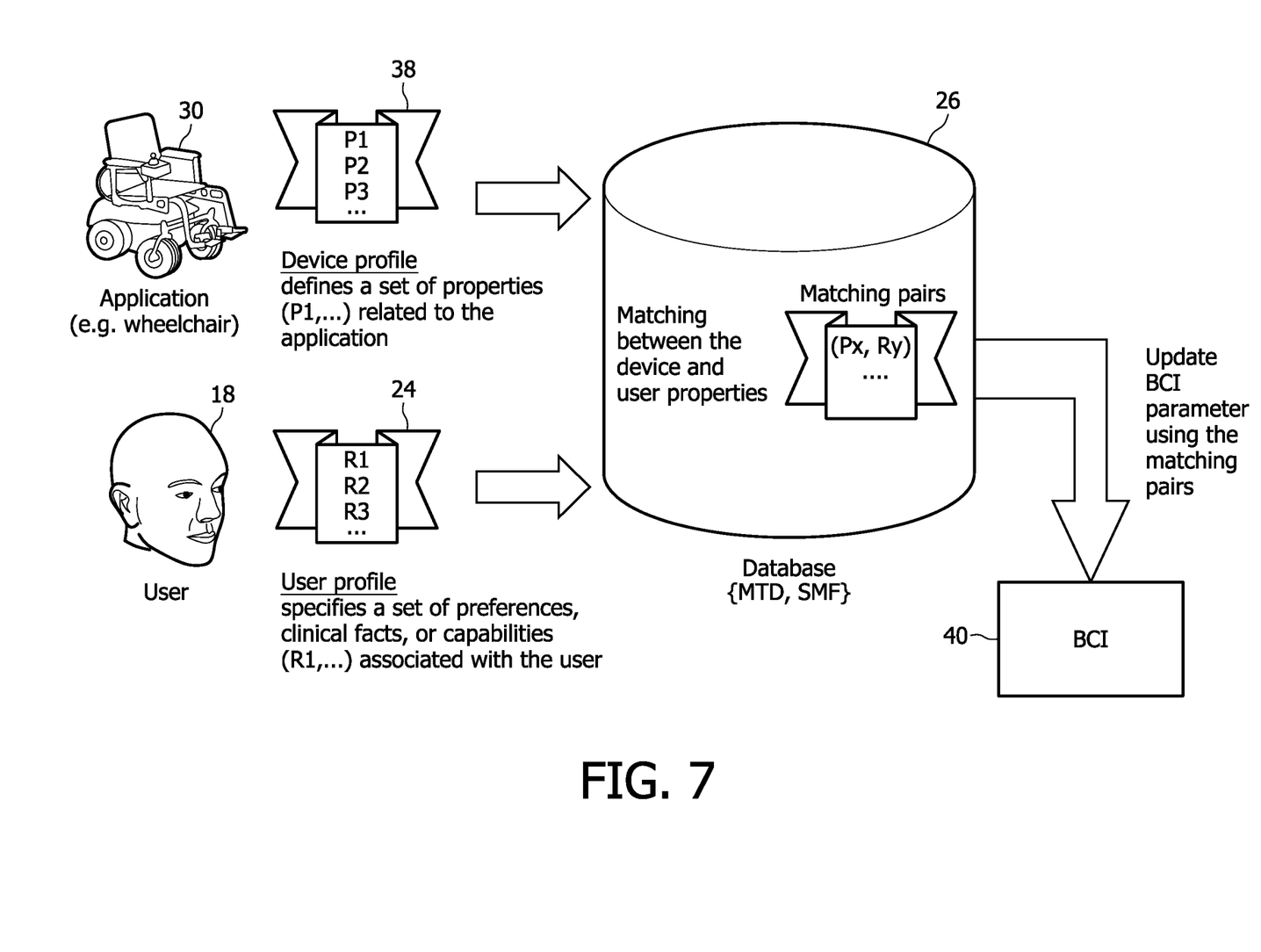
FIGS. 7 and 8 are schematic diagrams of a specific example of a BCI creation.

FIG. 7 shows the creation of a BCI 40 for a user 18 in relation to a specific application 34, which is the powered wheelchair 30. The user profile 24 that is associated with the user 18 and the application profile 38 that relates to the device 30 and the application that is controlling the device 30 are combined together in the processor 36 that is attached to the database 26. The matching occurs that links the properties P1 to Pn in the application profile 38 for the wheelchair 30 to the entries (or capabilities) R1 to Rm defined in the user's profile 24. As can be seen in the Fig., the properties and functions are paired up and this is used to generate the brain computer interface 40, that the user 18 can now use to control the wheelchair 30. The user 18 does not need to undergo any further or additional training to use the wheelchair 30, as the generation of the BCI 40 is based upon their known abilities, and is matched to that user's tasks.

Figure 8:
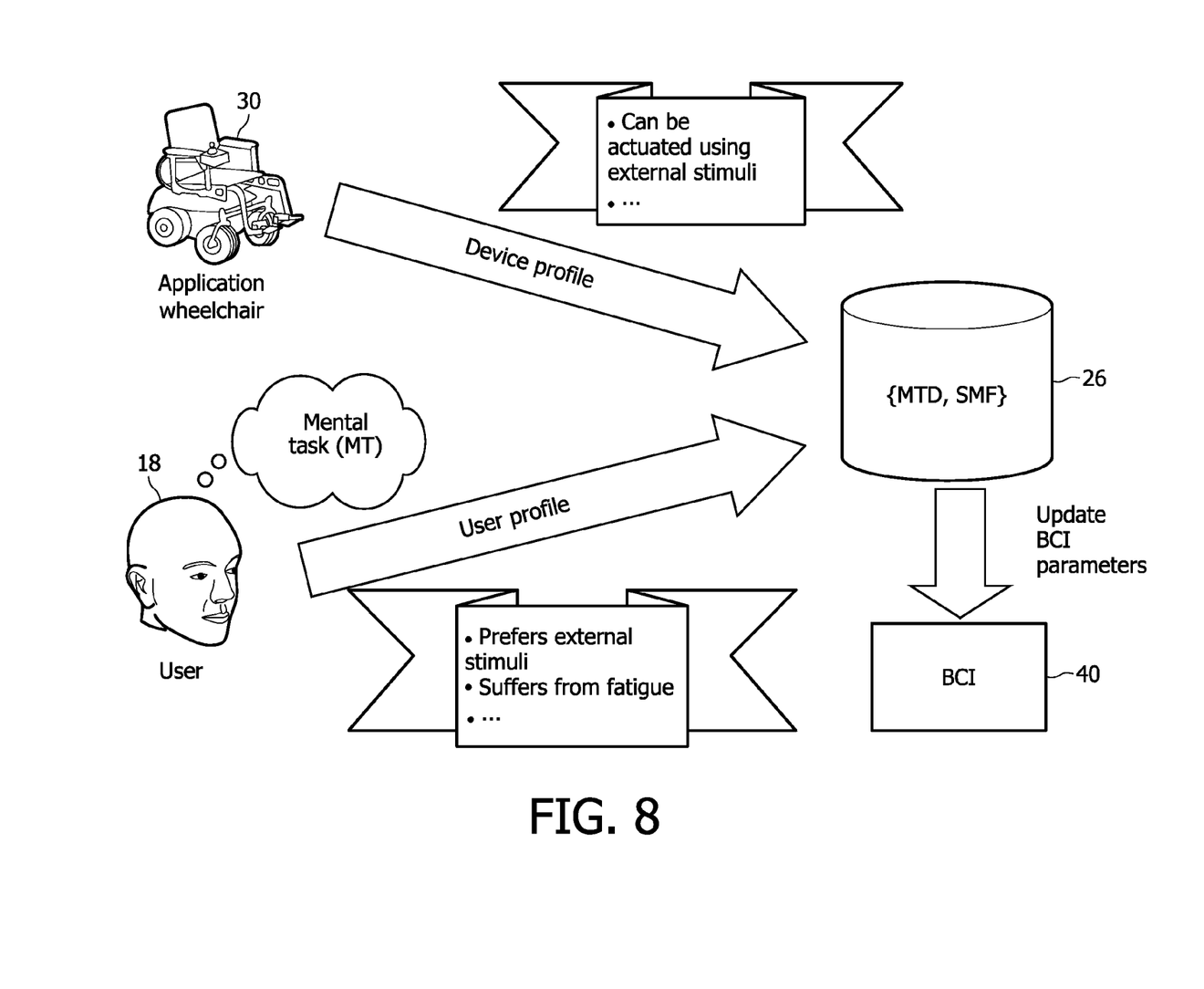

FIG. 8 shows a detailed example of the matching between the device properties (P1 to Pn) and the entries in the user's profile (R1 to Rm). The result of the matching is a set of pairs (Px1, Ry1) to (Pxk, Ryk) which are used to create the BCI 40. An example of matching can be: Pxk: this device 30 requires at least five commands (left, right, back, forward, and stop) and Pyk: this user can reliably perform five independent mental tasks.

The invention claimed is:

1. A method of creating a user profile for a brain computer interface, the method comprising the acts of:
   performing a training exercise;
   measuring a user's brain signals during the training exercise;
   mapping by a processor specific signals of the user's brain signals to predefined mental task descriptions;
   creating by the processor the user profile comprising the user's brain signals mapped to the predefined mental task descriptions;
   measuring a user's fatigue during the training exercise; and
   recording information relating to the measured fatigue in the user profile,
   wherein the user's fatigue is based on a number of times that the user can perform a specific mental task within a predefined accuracy resulting in a measured specific brain signal.

2. The method according to claim 1, further comprising an act of terminating the training exercise when the measured fatigue exceeds a predetermined threshold.

3. The method according to claim 1, further comprising the acts of:
   receiving manual input defining restrictions in relation to the predefined mental task descriptions; and
   recording the manual input in the user profile.

4. A system for creating a user profile for use in a brain computer interface comprising:
   a training unit configured to perform a training exercise;
   a head unit configured to measure a user's brain signals during the training exercise; and
   a processor configured to map specific signals of the user's brain signals to predefined mental task descriptions, to create the user profile comprising the user's brain signals mapped to the predefined mental task descriptions, to measure a user's fatigue during the training exercise, and to record information relating to the measured fatigue in the user profile wherein the user's fatigue is based on a number of times that the user can perform a specific mental task within a predefined accuracy resulting in a measured specific brain signal.

5. The system according to claim 4, wherein the processor is further configured to terminate the training exercise when the measured fatigue exceeds a predetermined threshold.

6. The system according to claim 4, further comprising a user interface configured to receive manual input defining restrictions in relation to the predefined mental task descriptions, wherein the processor is further configured to record the manual input in the user profile.

7. A non-transitory computer readable medium comprising computer instructions which, when executed by a processor, configure the processor to perform a method for creating a user profile for a brain computer interface, the method comprising the acts of:
   performing a training exercise;
   measuring a user's brain signals during the training exercise;
   mapping specific signals of the user's brain signals to predefined mental task descriptions;
   creating the user profile comprising the user's brain signals mapped to the predefined mental task descriptions;
   measuring a user's fatigue during the training exercise; and
   recording information relating to the measured fatigue in the user profile,
   wherein the user's fatigue is based on a number of times that the user can perform a specific mental task within a predefined accuracy resulting in a measured specific brain signal.

8. The non-transitory computer readable medium according to claim 7, wherein the computer instructions, when executed by the processor, further configure the processor to perform an act of terminating the training exercise when the measured fatigue exceeds a predetermined threshold.

9. The non-transitory computer readable medium according to claim 7, wherein the computer instructions, when executed by the processor, further configure the processor to perform the acts of:
   receiving manual input defining restrictions in relation to the predefined mental task descriptions; and
   recording the manual input in the user profile.

10. A method of creating a user profile for a brain computer interface, the method comprising the acts of:
    performing a training exercise;
    measuring a user's brain signals during the training exercise;
    mapping by a processor specific signals of the user's brain signals to predefined mental task descriptions;
    creating by the processor the user profile comprising the user's brain signals mapped to the predefined mental task descriptions;
    accessing the user profile comprising the user's brain signals mapped to the predefined mental task descriptions;
    accessing an application profile comprising a plurality of properties of the application;
    matching one or more of the predefined mental task descriptions from the user profile to a respective property from the application profile; and
    creating a brain computer interface based on results of the matching act.

11. The method according to claim 10, further comprising the acts of:
  accessing a fatigue component in the user profile; and
  adjusting the brain computer interface based on the fatigue component.

12. The method according to claim 10, and further comprising the acts of:
  accessing a manual input component in the user profile; and
  adjusting the brain computer interface based on the manual input component.

13. A system for creating a user profile for use in a brain computer interface comprising:
  a training unit configured to perform a training exercise;
  a head unit configured to measure a user's brain signals during the training exercise;
  a processor configured to map specific signals of the user's brain signals to predefined mental task descriptions, and to create the user profile comprising the user's brain signals mapped to the predefined mental task descriptions; and
  a database configured to store the user profile comprising the user's brain signals mapped to the predefined mental task descriptions and an application profile comprising a plurality of properties of the application,
  wherein the processor is further configured to access the user profile and the application profile, to match one or more of the predefined mental task descriptions from the user profile to a respective property from the application profile, and to create a brain computer interface based on results of the match.

14. The system according to claim 13, wherein the processor is further configured to access a fatigue component in the user profile and to adjust the brain computer interface based on the fatigue component.

15. The system according to claim 13, wherein the processor is further configured to access a manual input component in the user profile and to adjust the brain computer interface based on the manual input component.

16. A non-transitory computer readable medium comprising computer instructions which, when executed by a processor, configure the processor to perform a method for creating a user profile for a brain computer interface, the method comprising the acts of:
  performing a training exercise;
  measuring a user's brain signals during the training exercise;
  mapping specific signals of the user's brain signals to predefined mental task descriptions;
  creating the user profile comprising the user's brain signals mapped to the predefined mental task descriptions;
  accessing the user profile comprising the user's brain signals mapped to the predefined mental task descriptions;
  accessing an application profile comprising a plurality of properties of the application;
  matching one or more of the predefined mental task descriptions from the user profile to a respective property from the application profile; and
  creating a brain computer interface based on results of the matching act.

17. The non-transitory computer readable medium according to claim 16, wherein the computer instructions, when executed by the processor, further configure the processor to perform the acts of:
  accessing a fatigue component in the user profile; and
  adjusting the brain computer interface based on the fatigue component.

18. The non-transitory computer readable medium according to claim 16, wherein the computer instructions, when executed by the processor, further configure the processor to perform the acts of:
  accessing a manual input component in the user profile; and
  adjusting the brain computer interface based on the manual input component.

* * * * *